July 2, 1940. P. DOT Plant Pat. 407
ROSE PLANT
Filed Feb. 27, 1940
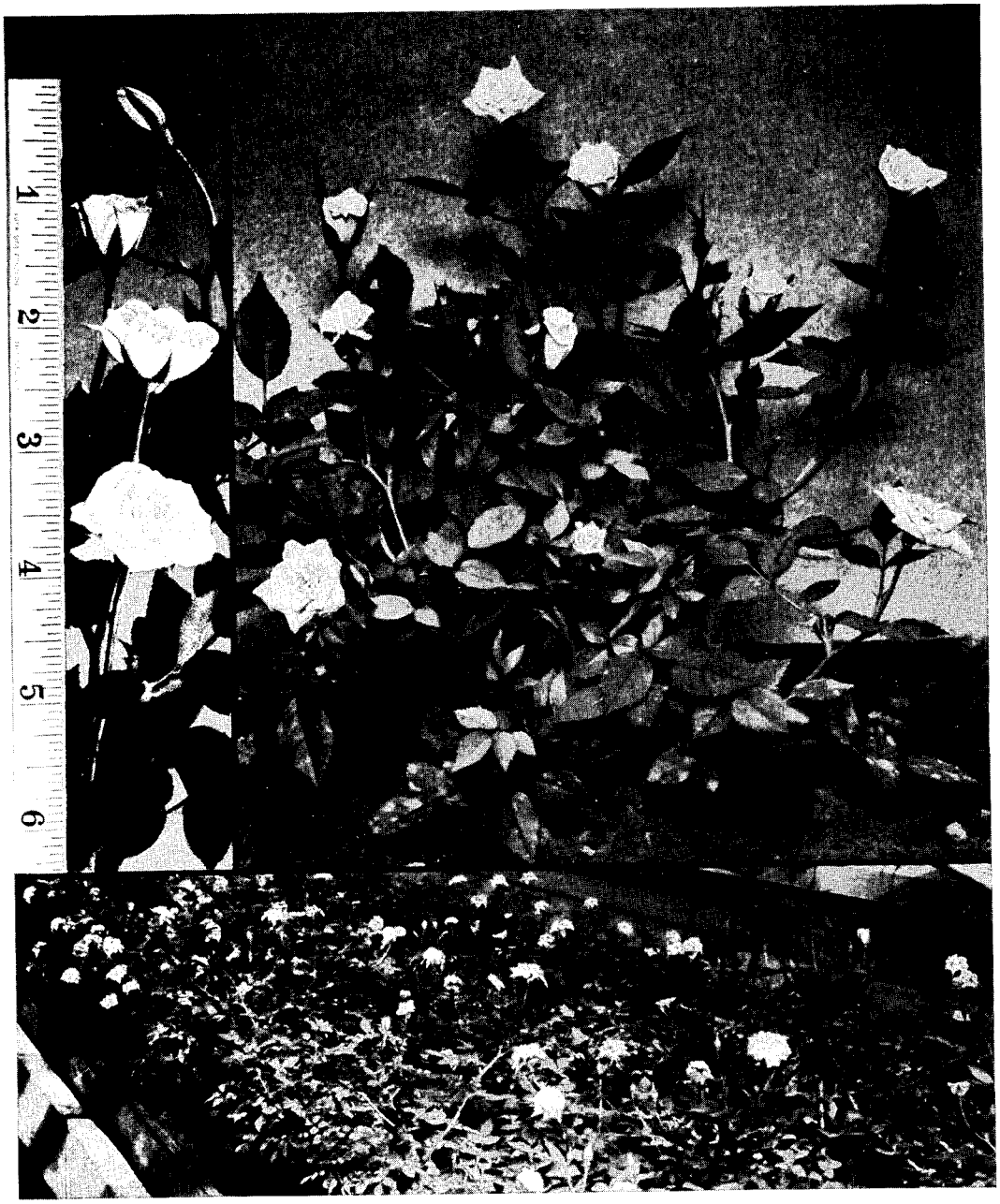
Inventor
Pedro Dot
By Robbins & Robbins
Attorneys Patented July 2, 1940

UNITED STATES PATENT OFFICE

407

ROSE PLANT

Pedro Dot, San Feliu de Llobregat, Spain, assignor to The Conard-Pyle Company, West Grove, Pa.

Application February 27, 1940, Serial No. 321,108

1 Claim. (Cl. 47—61)

The present invention relates to a new and distinct variety of rose plant of the Indica Minima species developed by me when the amount of space for the growing of flowers was greatly curtailed due to war conditions.

In the course of hybridizing of miniature roses, I was finally successful in the production of the present tiny yellow rose, the distinctiveness of which resides in the rare rich color in an exceedingly small bud and bloom on a small-size plant.

The novelty of this invention is presented primarily in the difference in size and shape of the leaf, the habit of growth, and the over-all size of the plant; and secondarily in the richness of the yellow coloring in nowise approached by any other tiny rose, the unusual perfection and exquisiteness of the form of the bud and the numerous character of the petalage, all combining in the production of a rose in a class by itself.

In the accompanying drawing, I have shown the color and various stages of development of the bloom from bud to full blown flower, an individual plant in association with a scale to show its habit of growth and normal size and in a bed showing the character of garden display obtainable with a rose of this type.

Asexual reproduction of the rose shows the characteristics referred to are fixed.

The following is a detailed description of this new rose, the color terminology employed therein being in accord with Ridgway's Color Standard.

Type: Half hardy to hardy; dwarf; greenhouse and outdoor; seedling; for cut flowers and garden decoration.

Class: Indica Minima.

Parentage:

*Seed parent.*—Eduard Toda.

*Pollen parent.*—Rouletti.

Propagation: It holds its distinguishing characteristics through succeeding propagations by cuttings.

*Flower*

Locality where grown: West Grove, Pennsylvania.

Flowers borne: Singly, on normal medium length stems.

Quantity of bloom: Free, outdoors and in greenhouse.

Continuity: Continuous.

Fragrance: Slight; tea.

Bud:

*Peduncle.*—Medium length; slender; bending; rough; numerous, Bice Green, Plate XVII; hairs, Victoria Lake colored, Plate I.

*Before calyx breaks.—Size*—five-eighths inches. *Form*—long, pointed with a conspicuous neck; without foliaceous appendages; with slender foliaceous parts extending beyond the tip of the bud equal to one-fourth or more of its length.

*As calyx breaks.—Color*—Primuline Yellow, Plate XVI, veiled with Apricot Orange, Plate XIV.

*As first petal opens.—Size*—small. *Form*—short, ovoid. *Color*—outside—Primuline Yellow, Plate XVI; inside—Cadmium Yellow, Plate III. *Opening*—opens up well.

Bloom:

*Size, when fully open.*—Small, one to two inches.

*Petalage.*—Semi-double; twelve to fifteen petals; arranged irregularly.

*Form.*—Open, cupped at first; becoming very flat and open; petals remaining loosely rolled outward; becoming later, at maturity, very loosely flat rolled outward.

Petals: Thin, soft, with inside and outside satiny.

*Shape.*—Obovate. Intermediate—round, obovate; Inside—obovate.

This description of a newly opened flower was made from a rose grown in a greenhouse, in September, 1939, at West Grove, Pennsylvania:

*Color.*—Outside petal: outside surface—Primuline Yellow, Plate XVI; inside surface—Cadmium Yellow, Plate III, pencilled and veiled with Rose Doree, Plate I. Intermediate petal: outside surface—Primuline Yellow, Plate XVI; inside surface—Cadmium Yellow, Plate III, pencilled and veiled with Rose Doree, Plate I. Inner petal: outside surface—Primuline Yellow, Plate XVI; inside surface—Cadmium Yellow, Plate III, pencilled and veiled with Rose Doree, Plate I.

This description was made from a rose that was open for three days in a greenhouse, in September, 1939, at West Grove, Pennsylvania:

*Color.*—Outside petal: outside surface—Napthaline Yellow, Strontian Yellow base, Plate XVI; inside surface—Light Napthaline Yellow, Strontian Yellow base, Plate XVI. Inside petal: outside surface—Napthaline Yellow, Strontian Yellow base, Plate XVI; inside surface—Light Napthaline Yellow, Strontian Yellow base, Plate XVI.

*General color effect.*—Newly opened flower—Primuline Yellow, Plate XVI. Three days open—Napthaline Yellow, Plate XVI.

*Behavior.*—Drop off cleanly.

*Flower longevity.*—On bush in garden, four days, in September; cut roses grown in greenhouse kept at living room temperature 4 to 5 days in September.

*Reproductive organs*

Stamens: Very few arranged regularly about pistils, mixed with petaloids.

Filaments: Short; Light Orange Yellow, Plate III; few with anthers.

Anthers: Very small; Light Cadmium, Plate IV.

Pollen: None showing.

Pistils: Few.

Styles: Short, thin, bunched.

Stigma: Orange Chrome, Plate II.

Ovaries: All enclosed in calyx.

*Plant*

Foliage:

*Leaves.*—Compound of three, five, seven; sparse; small; thin; soft.

*Leaflets.*—Ovoid to lanceolate with apex acute, base round; margin simply serrate.

*Color.*—*Mature:* upper surface—Leaf Green, Plate XLI; under surface—Asphodel Green, Plate XLI. *Young:* upper surface—Leaf Green, Plate XLI; under surface—Asphodel Green, Plate XLI.

*Rachis.*—(The supporting stem of the compound leaf) medium weight. Upper side—grooved, hairy; under side—sparsely prickly.

*Stipules.*—Long, narrow; with medium length points turning out at an angle of about 45°, recurved toward the stem.

*Disease.*—Subject to blackspot.

Growth:

*Habit.*—Dwarf, sprawling, little branched.

*Growth.*—Moderate.

*Canes.*—Medium heavy.

*Main stems.*—Pois Green, Plate XLI. *Thorns*—few, long, hooked downward, with short narrow base. *Prickles*—few; Etruscan Red, Plate XXVII. *Hairs*—none.

*Branches.*—Pois Green, Plate XLI. *Thorns*—few, medium length, hooked downward with short narrow base. *Prickles*—few; Orange Vinaceous, Plate XXVII. *Hairs*—none.

*New shoots*—Saccardo's Olive Green, Plate XVI. *Thorns*—few, medium length, both straight and hooked downward with short narrow base. *Prickles* — none. *Hairs* — none.

I claim:

A new and distinct variety of rose plant of the Indica Minima species, characterized by its habit of growth and size, the form and color of the bud and flower thereof, and the size and shape of leaf, substantially as shown and described.

PEDRO DOT.